Figure 1:
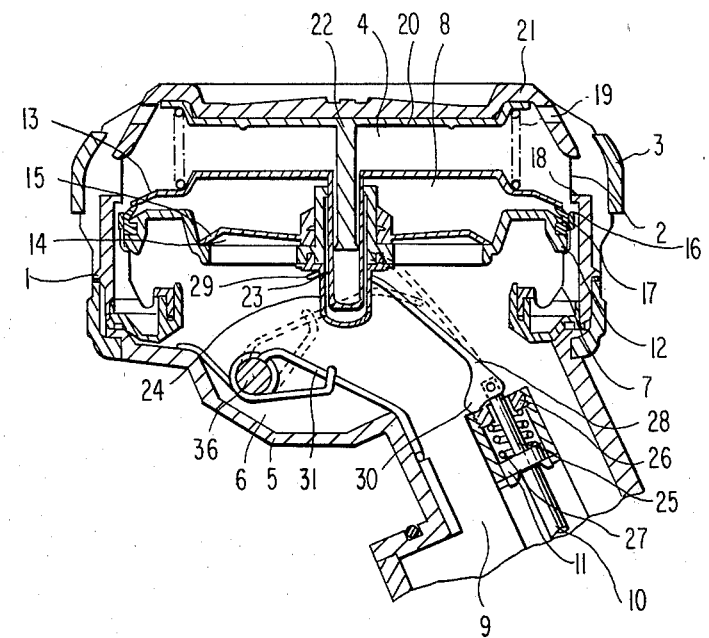

United States Patent [19]

Ekström et al.

[11] 4,361,145
[45] Nov. 30, 1982

[54] RESPIRATOR MASK

[75] Inventors: Staffan Ekström, Lidingö; Hans Wettergren, Södertälje, both of Sweden

[73] Assignee: AGA Aktiebolag, Lidingö, Sweden

[21] Appl. No.: 195,164

[22] Filed: Oct. 8, 1980

[30] Foreign Application Priority Data

Oct. 9, 1979 [SE] Sweden ............................ 7908339

[51] Int. Cl.³ .............................................. A62B 7/04
[52] U.S. Cl. ........................... 128/204.26; 137/DIG. 9
[58] Field of Search ...................... 128/204.26, 204.27, 128/200.27, 205.12, 206.24, 205.24, 207.12, 201.15, 206.15; 137/494, DIG. 9; 251/74

[56] References Cited

U.S. PATENT DOCUMENTS

| 2,406,888 | 9/1946 | Meidenbauer, Jr. | 128/205.24 |
| 3,680,555 | 8/1972 | Warncke | 128/206.24 |
| 3,716,053 | 2/1973 | Almovist et al. | 128/204.26 |
| 4,276,877 | 7/1981 | Gdulla | 128/200.27 |

FOREIGN PATENT DOCUMENTS 2620170 11/1977 Fed. Rep. of Germany ........................ 128/204.26
2735275 2/1979 Fed. Rep. of Germany ........................ 128/204.26

Primary Examiner—Henry J. Recla
Attorney, Agent, or Firm—Pollock, Vande Sande & Priddy

[57] ABSTRACT

A respirator mask that incorporates a respiration valve with a pressure chamber (8) between a breathing space (6) in front of the user's respiratory organs and the surrounding atmosphere. A gauge pressure in front of the user's respiratory organs during the inhalation phase as well as during the exhalation phase is established, whereupon a part of that side of the pressure chamber that faces towards the respiratory organs actuates an inhalation valve (11) in response to the movement of a regulating diaphragm (7), either directly or through a control unit (28). A detent mechanism (31), when engaged, acts counter to the regulating diaphragm (7) to detain the latter or the control unit (28) in a position in which the inhalation valve (11) is closed. When the wearer of the mask inhales, the detention provided by the detent mechanism is overcome by the force that the movement of the regulating diaphragm exerts upon the detent device during inhalation.

3 Claims, 2 Drawing Figures

U.S. Patent    Nov. 30, 1982    4,361,145

RESPIRATOR MASK

The present invention concerns a respiration valve.

In the case of respirator masks especially intended to be used in toxic atomospheres such as smoke-filled premises or for military use as a protection against poison gases, etc., it is desirable and necessary that there should be a slight amount of gauge pressure in the mask and valve during the inhalation phase as well as during the exhalation phase, since it is difficult to make a mask that will seal satisfactorily against faces of all shapes. This gauge pressure is provided by locating a pressure chamber between a space that is in direct communication with the respiratory organs of the person wearing the mask and the surrounding atmosphere. By means of a valve the pressure chamber is in direct communication with the space in front of the wearer's face during the exhalation phase. During the inhalation phase the valve is closed. To prevent generating too high a pressure in the pressure chamber the latter is in its turn provided with another valve which opens to the surrounding atmosphere when a pre-set pressure difference has been reached between the pressure chamber and the surrounding atmosphere. An inlet valve, which serves the purpose of admitting breathing gas from an inlet duct to the space in front of the wearer's respiratory organs, is open when the pressure in this space is lower than the pressure that is supposed to be present in the pressure chamber, and is otherwise closed. This means that the inlet valve will be closed during exhalation, when a higher pressure is present, and open during inhalation.

Since the gauge pressure is generated in the pressure chamber by the exhalations of the wearer, gas will flow out through the inlet valve when the gas mask is not being worn. Accordingly, facepieces of this type are sometimes provided with a manually operated control device by means of which the regulating device that determines the desirable pressure difference between the pressure chamber and the external atmosphere can be rendered inoperative. After this action, the inlet valve will open only if the pressure in the space in front of the wearer's face should go lower than the pressure of the surrounding atmosphere.

The inlet valve is thus closed when the facepiece is not being worn. If the facepiece is put on without the manually operated control device having been inactivated, the wearer can breathe out through the mask even if the safety pressure is not present.

This used to be regarded as an advantage, since when the gauge pressure is cut out the mask becomes somewhat easier to breathe than when the gauge pressure is present. The users of the masks have, when necessary, switched in the gauge pressure and checked that it was present by lifting the mask slightly away from the face. A loud exhaust hiss indicates the presence of a gauge pressure.

The circumstances in which these facepieces see service often impose a considerable mental strain. People are under stress and working against time, and decisions must be taken and acted upon without delay. In such situations a person who is to enter and work in a very toxic atmosphere forgets, in his haste, to switch the gauge pressure in again, since he has his mind on all the other things he has to do. This oversight can have disastrous results. Accordingly, the present invention sets out to provide a remedy for this drawback.

According to the invention, the respirator mask has been furnished with a detent mechanism, operable from outside, which can be used to switch out the gauge pressure. The detent mechanism is inactivated by means of an element which responds to the appearance of a pressure difference between the outside atmosphere and the space in front of the wearer's respiratory organs. As a result of this, the gauge pressure is automatically switched in when the user draws his first breath after putting the mask on. From then on, the gauge pressure is maintained continuously until the wearer engages the detent mechanism when he takes off the mask. The detent mechanism is actuated by a catch which is readily accessible and can be operated and checked from outside the mask.

Figure 2:
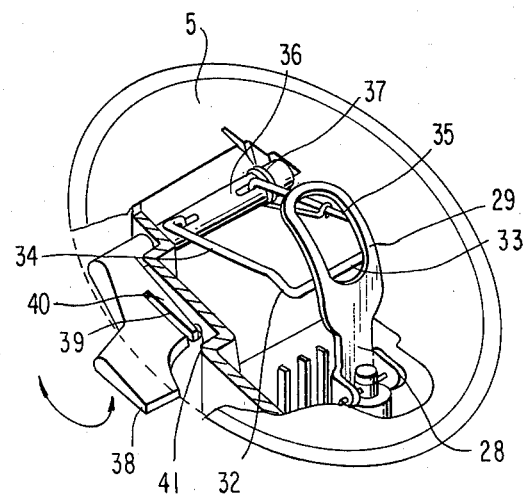

The invention is described more fully in the following embodiment with due reference to the accompanying drawings, of which FIG. 1 shows a cross-section through a form of realisation of the device and FIG. 2 is a perspective drawing of a form of realisation of the detent mechanism.

FIG. 1 shows one embodiment according to the invention. The respiration valve incorporates a substantially cup-shaped housing 1, which, close to the bottom part on the side wall, is furnished with a number of openings 2 in order to release the exhaled air to the surrounding atmosphere. A protective ring 3 is located around the housing opposite the openings 2 in order to protect the exhalation chamber 4 in the housing 1 from dust and outside influences. A funnel-shaped unit 5 is screwed onto the edge of the housing 1. An inlet chamber 6 is formed by the unit 5 and is delimited from the exhalation chamber 4 by a diaphragm 7 which has a pressure chamber 8. in its central region. The inlet chamber 6 is in direct communication with the space in front of the wearer's face through a communicating passage 9. An inlet duct 10 which admits the breathing gas is in communication with the inlet chamber 6 through an inlet valve 11. The pressure chamber 8 is designed as a movable unit, secured to the housing 1 through the movable diaphragm 7.

The pressure chamber 8 contains an inner, rigid, substantially dish-shaped part 12 and an outer, rigid, substantially dish-shaped part 13; the concave sides of these two parts face towards each other. Part 12 is provided with openings 14, which on the pressure-chamber side are covered with a disc-shaped exhalation valve 15.

The diaphragm 7 is made of a soft, flexible material such as rubber. At the annular attachment ends by which it is secured to the housing 1 and around the periphery of part 12 the material is thicker. Above part 12 the diaphragm part 7 is provided with an annular flange 16, running at an angle upwards and inwards, which seals against the periphery of the upper dish-shaped pressure-chamber part 13, so long as the gauge pressure in the chamber 8 does not exceed its predetermined level as determined by the gauge-pressure spring 19.

Outside the diaphragm part that is secured to part 12 is a retaining ring 17, which holds the diaphragm in place and is furnished with a lug, which when the pressure chamber moves outwards towards the exhalation chamber 4 is forced against an annular flange forming as integral part of the housing 1. The diaphragm 7 is thereby protected against stretching.

The upper dish-shaped part 13, which will be referred to from now on as the sealing disc, is forced against the annular flange 16 by a sealing spring 19, the other end of which is fixed to a guide plate 20 located right at the bottom 21 of the housing 1. The side of the guide plate that faces the bottom part of the housing is shaped to fit against it. The guide plate is provided at its centre with an inward-projecting guide pin 22. The sealing disc 13 is provided at its centre with an inward-projecting guide sleeve 23, which fits onto guide pin 22. In its turn, the guide sleeve 23 is inserted into a guide sleeve 24 which is made integral with part 12. The effect of this guidance arrangement is that parts 12 and 13 can move in one direction only, so that they are at all times parallel to the bottom part 21 of the housing 1.

The inlet duct 10 for breathing gas with valve 11 is installed in the tailpiece of the funnel-shaped part 5. The inlet valve 11 contains a disc which bears against a valve seat and is furnished with a rod 25, which projects into the inlet chamber 6 through a bush 26 which is in the form of a ring screwed into the end of a sleeve which forms a continuation of the inlet duct and has a larger diameter than the said duct. The inlet valve 11 is forced against the valve seat by a spring 27 between the valve 11 and the annular bush 26.

Pivoted to the upper end of the rod 25 is an arm 28, which normally runs at an angle in relation to the rod 25. The arm 28 has a bent upper end which rests against the inner part 12 of the pressure chamber and is provided with an opening 29, which is fitted around the guide sleeve 24. As can be seen in the perspective drawing in FIG. 2, the arm 28 is made out of a flat material. At the end in contact with the valve 11 the arm 28 is furnished with a projection 30, which, when the pressure chamber 8 moves in towards the inlet chamber 6, bears on the annular bush 26 and causes the valve 11 to lift. A detent unit 31 is so arranged that when engaged it lifts the arm 28 to the position shown by the broken lines, whereupon the opening 29 at the left-hand end of the figure moves to rest against the guide sleeve 24. Overcoming the spring 19, the pressure chamber 8 will then have been moved towards the bottom 21 of the housing and will be held there until the respirator mask is next put on by a user.

FIG. 2 shows a perspective view of the arm 28 with the detent device 31. This device comprises a slightly springy steel wire bail 32 which has a straight central section 33, which in the engaged position (shown in FIG. 2) bears against the arm 28. The two legs of the bail, 34 and 35, are bent off at right angles to the central section and are fastened at their ends to a rotary shaft 36. A spring 37 is coiled around the shaft 36. One end of it rests against the inside of the unit 5, while the other end is formed into a hook which bears against one leg 35 of the wire bail 32 and exerts upon it a force directed downwards in the figure. This spring 37 holds the unit 32 in the downward position, as shown in FIG. 1, when the detent device is disengaged.

One end of the shaft 36 passes through an airtight bush in the wall of unit 5 and is fitted on the outside of the respirator mask with a lever 38, by means of which the wearer of the mask can readily turn the shaft, i.e. can activate or disengage the detent mechanism. The lever is angled transverse to the shaft. Also angled transverse to the shaft and separated from the lever by a slit is a catch 40. It consists of a sprung arm bearing against the wall of unit 5 and fitted at its free end, on the side facing the wall, with a boss 41, which, when the catch is on, slips into a recess provided for it in the wall of the unit 5. The force which is needed to shift the boss out of the recess by twisting shaft 36 is gauged to correspond to the force with which the pressure chamber acts upon the wire bail 32, via the arm 28, when the wearer of the mask inhales. After the detent device has been released by an inhalation the wire 32 is moved by the spring 37 to bear against the side of unit 5 (see FIG. 1). The lever 38 will thereby be turned to point downwards in the figure. It is easy for the user of the mask to ascertain whether the detent device really has released by checking the position of the lever.

Many modifications of the invention as defined by the claims which follow will of course be possible.

We claim:

1. A respirator mask comprising:
    a housing including an exhalation chamber having an exhaust outlet, and an inlet chamber forming a breathing space and having passage means adapted to communicate with a user's respiratory organs;
    a normally closed inlet valve connected to said inlet chamber for supplying a source of breathing air to the inlet chamber to provide pressure therein;
    means for establishing a gauge pressure in said inlet chamber including a movable member mounted in said housing and separating said inlet chamber from said exhalation chamber, biasing means biasing said movable member toward said inlet chamber, means operatively associated with said movable member for actuating said inlet valve to supply pressure to said inlet chamber when said movable member is moved into said inlet chamber and for releasing pressure from said inlet chamber to said exhaust outlet when said movable member is moved into said exhalation chamber a predetermined distance wherein a gauge pressure is established and released in said inlet chamber in response to movement of said movable member; and
    detent means mounted in said housing for moving and maintaining said movable member towards said exhalation chamber against said biasing means whereby said inlet valve means is maintained in its closed position, said detent means including means for releasing said movable member in response to a user's inhalation effort in said inlet chamber whereby said inlet valve opens and said gauge pressure is re-established.

2. A respirator mask according to claim 1, wherein the detent means is provided with a control lever outside the housing, which enables the state of the means to be readily checked by the user.

3. A respirator mask according to claim 1 or claim 2, wherein the detent means incorporates a bail that acts upon said diaphragm said bail being attached to a spring-loaded rotary shaft to which is secured an arm, said arm exerting a spring pressure against said housing of the respirator mask and is provided with a boss which in the detention position fits into a recess in the wall maintaining said diaphragm deflected towards said exhalation chamber.

* * * * *